United States Patent [19]
Able

[11] Patent Number: 6,000,402
[45] Date of Patent: Dec. 14, 1999

[54] PROTECTIVE ARM AND LEG RESTRAINT

[76] Inventor: Heather Michelle Able, 2156 Medway Rd., Charleston, S.C. 29412

[21] Appl. No.: 09/126,350

[22] Filed: Jul. 30, 1998

[51] Int. Cl.$^6$ .................................................. A61B 19/00
[52] U.S. Cl. ......................... 128/869; 128/878; 128/882; 602/20
[58] Field of Search ................................... 128/846, 869, 128/877, 878, 879; 602/4, 5, 20, 21, 23

[56] References Cited

U.S. PATENT DOCUMENTS

| | | | |
|---|---|---|---|
| 1,635,230 | 7/1927 | Spicer | 602/5 |
| 2,279,296 | 4/1942 | Bresnick et al. | 128/133 |
| 2,468,580 | 4/1949 | Weis et al. | 273/35 |
| 2,655,916 | 10/1953 | Timmins | 602/4 |
| 3,462,764 | 8/1969 | Caster | 2/252 |
| 3,533,407 | 10/1970 | Smith | 128/165 |
| 3,939,829 | 2/1976 | Spann | 128/878 |
| 4,206,512 | 6/1980 | Osborne | 2/69.5 |
| 4,379,463 | 4/1983 | Meier et al. | 128/80 |
| 4,470,410 | 9/1984 | Elliot | 128/133 |
| 4,481,942 | 11/1984 | Duncan | 128/133 |
| 4,489,718 | 12/1984 | Martin | 128/80 |
| 4,615,339 | 10/1986 | Siwek | 128/133 |
| 4,941,464 | 7/1990 | Scott | 128/84 |
| 4,941,479 | 7/1990 | Russell et al. | 128/877 |
| 4,971,041 | 11/1990 | Millikran | 128/878 |
| 5,131,412 | 7/1992 | Rankin | 128/877 |
| 5,279,574 | 1/1994 | Forren | 604/174 |

*Primary Examiner*—Michael A. Brown
*Attorney, Agent, or Firm*—Harleston Law Firm; Kathleen M. Harleston

[57] ABSTRACT

A soft, removable, protective restraint device for the arm or leg of a person, comprising:

(a) at least two bands including a wrist band having a circumference slightly greater than that of the person's wrist area, and an upper arm band having a circumference slightly greater than that of the person's upper arm area;

(b) a plurality of lock and loop portions for removably fastening one end of each band to an opposite end of the same band;

(c) between about one and ten longitudinally oriented bars attached at each end to the bands; each bar being parallel to the other and evenly spaced;

(d) an equal number of lightweight stiffening members; each bar comprising an enclosed stiffening member; and (e) a soft, sturdy, washable fabric substantially covering the device is provided.

The restraint device has an open position and a cylindrical closed position when the loop portions are fastened to the corresponding lock portions on each band; and wherein the restraint device in the closed position fits comfortably but snugly in a generally cylindrical configuration around an arm or leg of the person.

13 Claims, 2 Drawing Sheets

PROTECTIVE ARM AND LEG RESTRAINT

TECHNICAL FIELD

The present device is a protective restraint for removable placement around a person's arm or a leg, particularly the arm of an infant post-surgical patient.

BACKGROUND INFORMATION

Having a seriously ill or injured child is one of the great fears of parenthood. Seeing one's offspring, particularly an infant, laying in a hospital bed covered in bandages and surrounded by tubing and medical equipment is a terrible experience. One small thing that can be done to ease the discomfort of such pediatric patients is to create a restraint device which is effective, yet not oppressive in presence or appearance.

Restraints are often placed by hospital personnel on a pediatric or geriatric patient's arms to prevent him or her from pulling at the bandages and surrounding equipment. Many currently available restraint devices cover most of the patient's arm, and are stiff and uncomfortable. A child's skin underneath such devices often becomes sweaty and itchy. Some currently available one-piece restraints are generally cylindrical and have the same circumference at the top and bottom of the device, so the child's arm movements work the device off at the wrist. For that reason, some available two-arm devices have an uncomfortable strap attached to the tops of two cast-like arm restraints which extend over the wearer's shoulders and behind his or her neck. Some cast-like restraint devices extend down over the wearer's hand and have a very uncomfortable thumb hole. Some current restraint devices have string ties which are fastened around the device on the arm. These ties often loosen or untie and must frequently be retied. Many available devices are bulky and hard to put on the child. There is also a need for a restraint device that is easy to put on and take off, and does not slide around on the small arm of a baby. The device of the present invention solves these problems.

The present device is particularly well-suited for use on an infant's arms after cranial, facial or upper body surgery. The device prevents the infant's arm from bending at the elbow. It is particularly useful for infants who have had cleft lip and palate operations to keep the infant or older child from touching or inadvertently pulling out stitches, bandages, oxygen tubes, intravenous devices, and other medical aids. It also keeps the baby from putting objects into its mouth. It may be used for several days or weeks after surgery, and can be removed periodically for cleaning the device or the child. It can also be used on patients who have had eye surgery, tracheotomies, or who have burns on the head, face or upper body, to reduce infections and prevent removal of tubes or bandages.

In addition to post-surgical use, the present device can be used in intensive care units for restraining the arms of injured or ill patients, particularly those who are confused or delirious. It can be used in emergency situations for restricting the movement of frightened children with, for example, foreign items lodged in their eye or nose, or for flushing of small children's ears. The present device can be employed to restrict movement of a sprained or strained knee or elbow, or an arm or leg that has been otherwise cut or injured, for in- or out-patients of various ages. It can be used in the course of physical therapy for supporting the bones and muscles of the legs or arms, or to brace a young child's legs to assist in walking. It can be used to restrain arm or leg movement while X-rays are being taken. It can be used on the arms of children to restrict scratching of rashes such as chicken pox, thus minimizing scarring, or to help prevent thumb-sucking. With the addition of ties or loops on the wrist band, this device can be used on the arms and/or legs of a delirious, senile, or semi-conscious person for restraining him or her in bed in, for example, a hospital, nursing home, hospice or private home.

BRIEF SUMMARY OF THE INVENTION

The present device is a soft, removable, protective restraint device for the arm or leg of a person, preferably for use on an infant's arm post-surgery. This device comprises:

(a) at least two bands, each with a length dimension which is substantially greater than its width dimension; the bands comprising a lower band having a circumference slightly greater than that of the person's wrist or ankle area, and an upper band having a circumference slightly greater than that of the person's upper arm or thigh area;

(b) a plurality of lock and loop portions for removably fastening one end of each band to an opposite end of the same band;

(c) between about one and ten bars; each bar being connected at opposite ends to the upper and lower bands; the bars being longitudinally oriented and approximately parallel to each other and occurring at approximately equal intervals along the upper and lower bands; the bars being approximately perpendicular to the upper and lower bands; the bands running approximately parallel to each other; each bar having a length dimension which is substantially greater than its width dimension; the length dimension being less than the length of the person's arm or leg, and greater than the length of the person's forearm or lower leg;

(d) an equal number of lightweight stiffening members; each bar comprising an enclosed stiffening member; the stiffening member being sufficiently rigid to resist bending in a direction perpendicular to the axis of the bar; and (e) a soft, sturdy, washable fabric substantially covering the device.

The restraint device remains intact and comfortable to wear after repeated washing in hot water and drying in a clothes dryer. It has an open position and a cylindrical closed position when the loop portions are fastened to the corresponding lock portions on each band. In the closed position, it fits comfortably but snugly in a generally cylindrical configuration around an arm or leg of the person.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein.

DETAILED DESCRIPTION OF THE INVENTION

Figure 1:
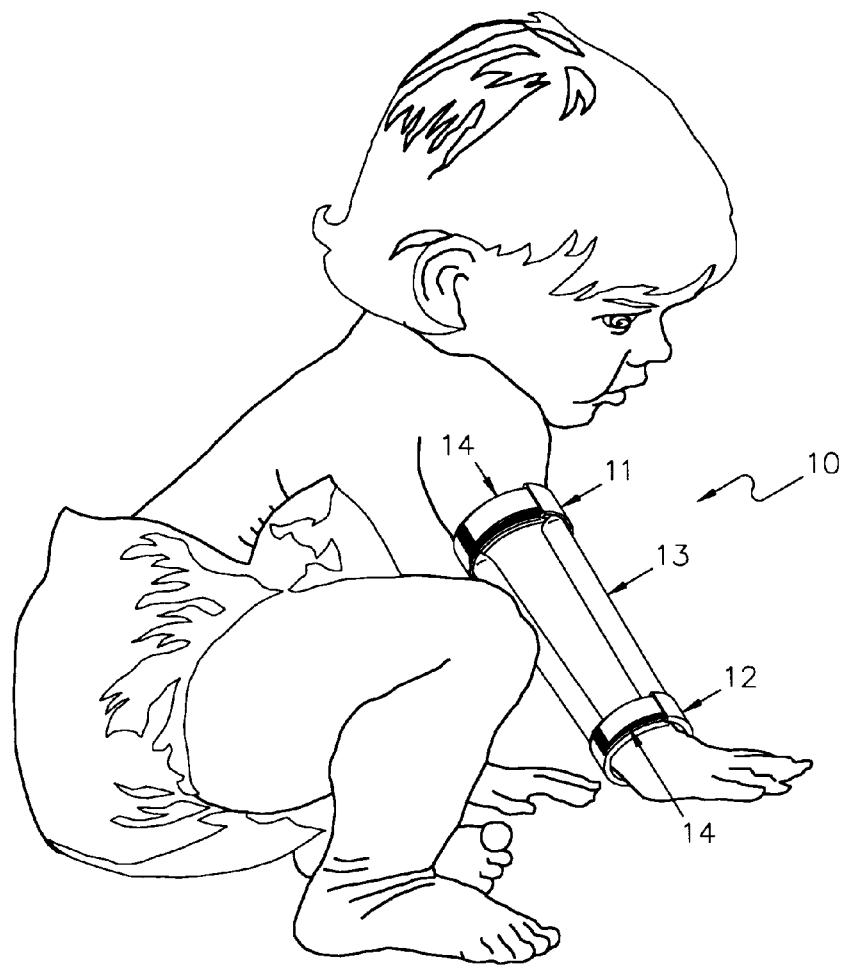
FIG. 1 is a perspective view of a restraint device according to the present invention.

In the following description, like reference characters designate like or corresponding parts throughout the several views. Also, in the following description, it is to be understood that such terms as "front," "back," within," and the like are words of convenience and are not to be construed as limiting terms. Referring in more detail to the drawings, the invention will now be described.

Referring to FIG. 1, a preferred embodiment of a restraint device 10 includes two bands: an upper arm band 11, and a lower wrist band 12. The upper arm band is longer than the wrist band to accommodate the greater circumference of the child's upper arm. Three longitudinally oriented bars 13 are sewn at opposite ends to the upper and lower bands 11, 12. Up to eight or ten bars could be included for older patients, but three or four bars are preferred. The bars 13 are approximately parallel to each other and are placed at approximately equal intervals along the bands 11, 12.

Figure 2:
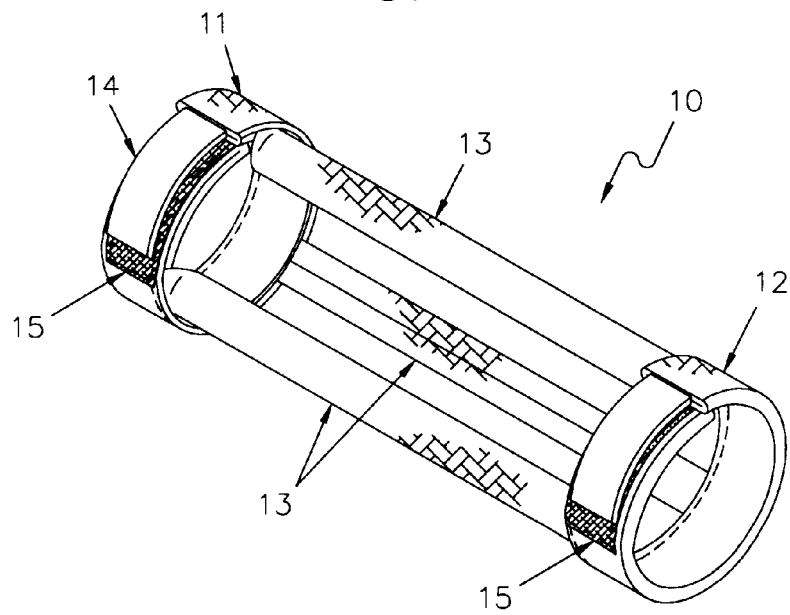
FIG. 2 is a perspective view of a restraint device according to FIG. 1 in the closed position.

As shown in FIG. 2, the bands are removably fastened around the child's arm by means of lock and loop portions 14, 15. The present device is ideally made in various band and bar lengths, to accommodate different sized children, although the lock and loop portions allow some latitude in fit. The restraint device is preferably placed on the arm with the lower band being fastened around the wrist area. The upper arm band can be fastened in the mid-bicept area or closer to the under arm. In a less preferred embodiment, the present device can be used entirely on the lower arm (half arm) for some uses such as restraining a geriatric patient in a bed. In a less preferred embodiment, the present device is fastened on the leg, with the lower band at the ankle, or mid-calf, and the upper band being fastened at mid-thigh.

Figure 3:
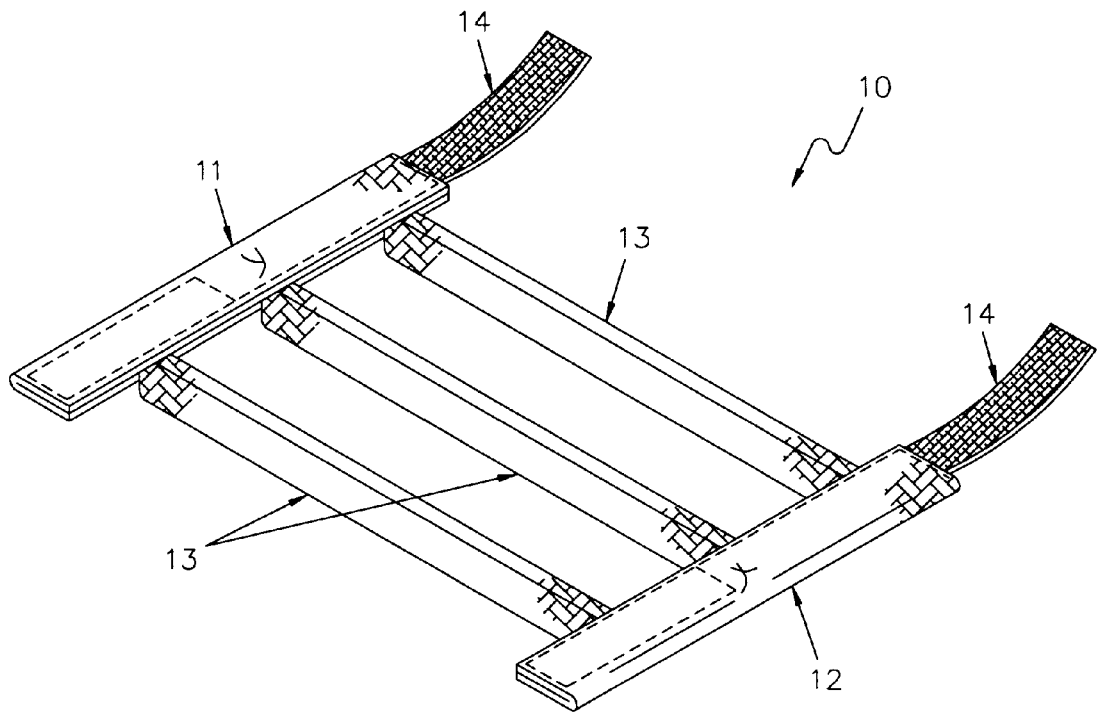
FIG. 3 is a perspective view from the bottom of a restraint device according to FIG. 1, shown in the open position.

The device 10 is shown in the closed, fastened position in FIGS. 1 and 2, and in the open, flat position in FIG. 3. FIG. 3 shows the device from the bottom perspective, which is the side of the device which lies against the arm when the device is in the closed position. No sharp or coarse areas lie against the skin, and the device is substantially covered with a soft, sturdy, washable fabric so that it is comfortable and absorbent The fabric preferably covers all points of contact between the restraint device and the baby's arm. Cotton flannel and terry cloth are preferred.

Figure 4:
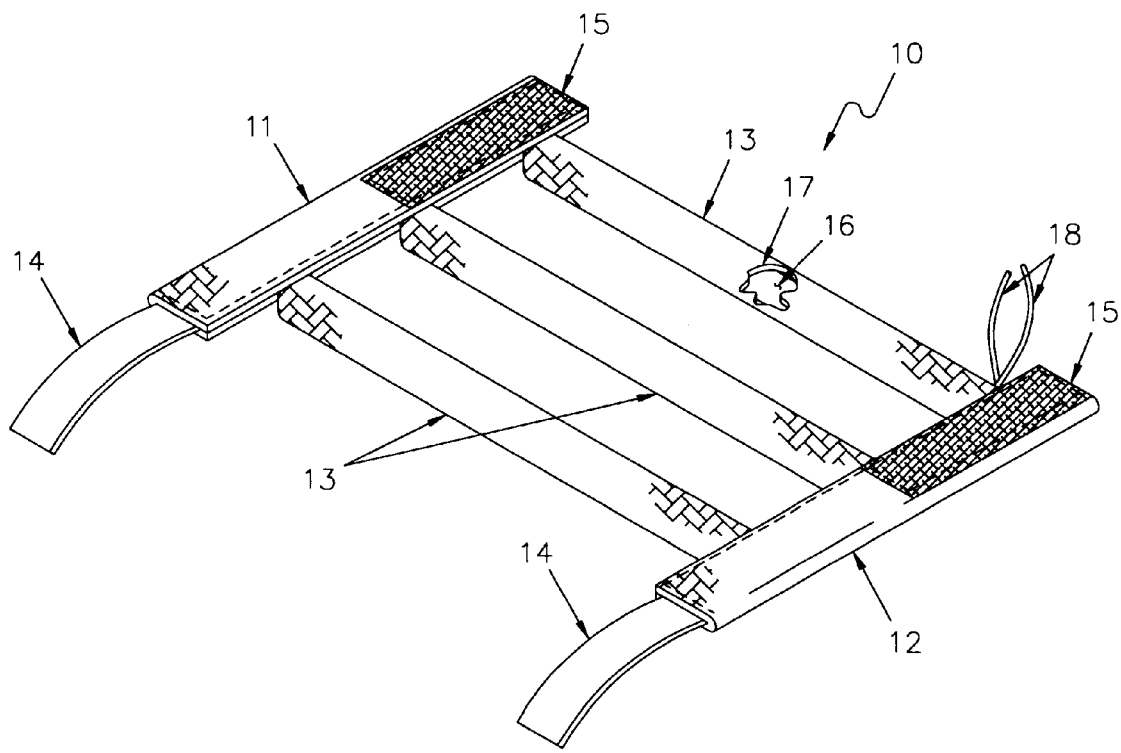
FIG. 4 is a perspective view from the top of a restraint device according to FIG. 1, shown in the open position.

As shown in FIGS. 3 and 4, the lock portions (strips) 15 are sewn onto the end portions of the bands 11, 12, and the loop strips 14 are sewn into the seams of the bands on the opposite ends of the bands. The ends of the fabric covering the bars 13 are sewn into the side seams of the bands 11, 12 for durability. FIG. 4 shows the device from the top. In use, each loop strip 14 is placed over the corresponding lock strip 15 on the other end of the same band. Inside each bar 13 of the device is a lightweight stiffening member 16. Each stiffening member is sufficiently rigid to resist bending in a direction that is perpendicular to the axis of the bar. The stiffening members are preferably lightweight wooden dowels or plastic rods, that are most preferably covered with a cushioning material 17 such as foam before the bars are covered with the washable fabric. The restraint device remains intact and comfortable to wear after repeated washing in hot water and drying in a clothes dryer.

Although the present device is preferably for use on babies, particularly on infants post-surgery, it is also suitable for use on some geriatric or semi-conscious patients. Workers in hospitals, nursing homes, hospices, and even in individual homes often find it necessary to restrain delirious, senile, semi-comatose, or otherwise disoriented in- or out-patients, including some very elderly individuals, to protect them from harm. Without restraints, such patients may pull out intravenous devices, nasogastric tubes, oxygen tubes, or other medical devices or treatments, fall during attempts to get out of bed, or become confused and wander outside. This is particularly true at night when there are fewer sitters available to keep an eye on these patients. The present device is suitable for use on the arm or leg of a delirious, senile, or semi-conscious in- or out-patient.

The present device has an open position when laid flat and a cylindrical, closed position when the attachment means are fastened on each band. The restraint device in the closed position fits comfortably but snugly around one arm of the patient. Once it is fastened, it will not slip off. The restraint device preferably surrounds a portion of the patient's arm or leg around the elbow or knee and prevents the patient's arm or leg from bending, thus limiting the patients range of movement.

The restraint device preferably further comprises a second, removable attachment means 18 for attaching the restraint device, and therefore the arm or leg of the patient, to a bed rail. The means for attachment to the bed rail is preferably a loop or a cloth or string tie. When these restraint devices are placed on both arms or legs of a patient, they help to immobilize the patient for the period of impairment.

In a preferred embodiment for use on an infant, the bands of the device are between about ¼ and eight inches, more preferably between about four and six inches, in length, and between about ¼ and two, more preferably ½ and one, inches in width, and the upper arm bands are preferably longer than the wrist bands.

From the foregoing it can be realized that the described device of the present invention is effective in restraining the arms of a small child, for example, yet it is soft, relatively flexible, and comfortable. It can therefore be used long-term on a person, with periodic removal for cleaning. The present device, which when closed is generally cylindrical, includes upper and lower bands which fit around the baby's arm. The device of this invention does not slide loosely around on a child's arm, and frequent retying is not necessary. This device employs lock and loop attachment means, which are safer and quicker than strings. Less preferably, the lock and loop attachment means could be modified, or an alternate attachment means substituted, for use on older children or adults.

Rather than substantially covering the arm, the present device includes several evenly spaced, longitudinally oriented bars so that the child's arm may still be seen and stroked. The spacing between the bars allows for air circulation and sensation on the wearer's arms. This is both a physical and psychological benefit for a pediatric patient and his or her parents as it ameliorates the trauma of having restraint devices on the child's arms. Having the area covered by the restraint device visible to the patient, parents and healthcare workers can also be important. Any developing skin problems, lesions, or pinched areas are also more visible because the present device does not cover the whole arm area.

In use, one of these devices can be quickly and easily fastened on each arm of the infant or other wearer. The device does not press into or pinch the skin of the patient as many currently available devices do. The skin of the arm underneath the device is also kept cooler and does not become itchy and sweaty. This device is not bulky and may be worn under or over clothing. The device can be made in several standard sizes, or it can be custom-made to fit the individual child's arm, including chubby children. Unlike some currently available devices, a patient can wear one of the present restraint devices on each arm without requiring a strap attached to the tops of the devices and extending over the petient's shoulders and behind his or her neck. An uncomfortable thumb hole is not required; the present device stays on the arm of even a small premature infant. On some currently available devices, the top of the restraint falls just under the wearer's arm, which is uncomfortable. The top of the present device can fit over the bicept area, which is more comfortable.

With the restraint device of the present invention, the wearer's arm is free for insertion of an intravenous device (IV). This is particularly advantageous for infants and older babies because it is often difficult to find (insert an intravenous needle in) a baby's small veins; the present device frees the baby's arms for intravenous device placement. The present restraint device may even prove helpful in holding the child's arm straight so that a vein may be more easily and safely located and punctured by the phlebotomist. With the present restraint device, an intravenous device, including the intravenous needle and/or catheter and tubing, in the child's arm is visible. Thus, trouble with the intravenous device can be spotted by the patient or adults in the hospital room. For example, a bubble forming in the intravenous tubing, an intravenous needle which has worked its way out of the blood vessel, and leakage from the intravenous device or puncture wound would be seen more easily when the present restraint device is employed. Tubing from the intravenous device can be threaded through the lock and loop attachment on either band to better hold the tubing in place. If desired, the device can be modified to cover or hold the intravenous device.

The device of the present invention could similarly be used, with or without modification, on the arms or legs of other mammals, e.g., during an operation on a zoo primate. This device can even conceivably be employed as a practice device to brace a person's arm or leg in a straight position, such as a golf swing improvement practice device to hold a golfer's arm (or leg) straight.

While preferred embodiments of the invention have been described using specific terms, this description is for illustrative purposes only. It will be apparent to those of ordinary skill in the art that various modifications may be made without departing from the spirit or scope of the invention, and that such modifications are intended to be within the scope of the present invention.

What is claimed is:

1. A soft, removable, protective restraint device for the arm or leg of a person, the restraint device comprising:

(a) at least two bands, each with a length dimension which is substantially greater than its width dimension; the bands comprising a lower band having a circumference slightly greater than that of the person's wrist or ankle area, and an upper band having a circumference slightly greater than that of the person's upper arm or thigh area;

(b) a plurality of lock and loop portions for removably fastening one end of each hand to an opposite end of the same hand;

(c) between about one and ten bars; each bar being connected at opposite ends to the upper and lower bands; the bars being longitudinally oriented and approximately parallel to each other and occurring at approximately equal intervals along the upper and lower bands; the bars being approximately perpendicular to the upper and lower bands; the bands running approximately parallel to each other; each bar having a length dimension which is substantially greater than its width dimension; the length dimension being less than the length of the person's arm or leg, and greater than the length of the person's forearm or lower leg;

(d) an equal number of separate lightweight stiffening members; each bar comprising an enclosed stiffening member; the stiffening member being sufficiently rigid to resist bending in a direction perpendicular to the axis of the bar; and (e) a soft, sturdy, washable fabric substantially covering the device; and wherein the restraint device, which does not include a thumb hole, is quickly and easily applied to the arm or leg of a persons and remains intact and comfortable to wear after repeated washing in hot water and drying in a clothes dryer; and wherein the restraint device has an open position and a cylindrical closed position when the loop portions are fastened to the corresponding lock portions on each band; and wherein the restraint device in the closed position fits comfortably but snugly in a generally cylindrical configuration around an arm or leg of the person.

2. A device according to claim 1 for use on a person's arm, wherein each bar further comprises cushioning material around the stiffening member for comfort.

3. A device according to claim 2 for quick and easy application on the arm of a person, wherein the device comprises two bands and between two and four bars.

4. A device according to claim 3 for use on a pediatric patient's arm after surgery, wherein the device surrounds a portion of the patient's arm around the elbow and prevents the arm from bending, thus restricting movement of the patient's hand.

5. A device according to claim 4 for use on the arm of an infant after cranial or facial surgery, wherein the bands of the device are each between about ¼ and eight inches in length, and between about ¼ and two inches in width, and wherein the upper arm bands are longer than the wrist bands.

6. A device according to claim 4, wherein the stiffening members are lightweight wooden dowels or plastic rods.

7. A device according to claim 2, wherein the restraint device further comprises a second, removable attachment means at the wrist band suitable for attaching the device, and therefore the arm or leg in it, to a bed rail.

8. A device according to claim 7 for use on the arm or leg of a delirious, senile, or semi-conscious person, wherein the wrist band further comprises a string or cloth tie, and wherein devices on both arms or legs of a patient and tied to a bed rail help to immobilize the patient.

9. A device according to claim 2 for quickly restricting the movement of frightened children during medical treatment.

10. A device according to claim 2 for holding a pediatric or geriatric patient's arm in one place during venipuncture.

11. A device according to claim 2 for supporting an intravenous device in the arm of a pediatric or geriatric patient while restraining movement of the arm.

12. A device according to claim 1 for bracing the legs of a child for assistance in walking.

13. A device according to claim 1 for use as a golf swing improvement practice device to brace an adult's arm or leg in a straight position.

* * * * *